US00PP27134P2

(12) United States Plant Patent
Meinl

(10) Patent No.: US PP27,134 P2
(45) Date of Patent: Sep. 6, 2016

(54) ***HYDRANGEA* PLANT NAMED 'SAXREB13'**

(50) Latin Name: *Hydrangea macrophylla*
Varietal Denomination: Saxreb13

(71) Applicant: Katrin Meinl, Dresden (DE)

(72) Inventor: Katrin Meinl, Dresden (DE)

(73) Assignee: Kühne Jungpflanzen Claus + Torsten Kühne Gbr, Dresden (DE)

( * ) Notice: Subject to any disclaimer, the term of this patent is extended or adjusted under 35 U.S.C. 154(b) by 158 days.

(21) Appl. No.: 14/121,802

(22) Filed: Oct. 20, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'Saxreb 13', characterized by its upright and mounded plant habit; moderately vigorous to vigorous growth habit; strong stems; and large mophead-type inflorescences with red purple-colored sterile flowers that are initially light green and red purple in color during early development.

3 Drawing Sheets

Botanical designation: *Hydrangea macrophylla.*
Cultivar denomination: 'SAXREB13'.

BACKGROUND OF THE INVENTION

The present invention relates to a new and distinct cultivar of *Hydrangea* plant, botanically known as *Hydrangea macrophylla* and hereinafter referred to by the name 'Saxreb13'.

The new *Hydrangea* plant is a product of a planned breeding program conducted by the Inventor in Dresden, Germany. The objective of the breeding program was to develop new container-type *Hydrangea* plants with strong stems, early flowering response and attractive leaf, stem and flower coloration.

The new *Hydrangea* plant originated from a cross-pollination in 2006 of two unidentified proprietary selections of *Hydrangea macrophylla*, not patented. The new *Hydrangea* plant was discovered and selected by the Inventor in 2008 as a flowering plant from within the progeny of the stated cross-pollination in a controlled greenhouse environment in Dresden, Germany.

Asexual reproduction of the new cultivar by softwood cuttings in Dresden, Germany since June, 2008 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Saxreb13'. These characteristics in combination distinguish 'Saxreb13' as a new and distinct *Hydrangea* plant:

1. Upright and mounded plant habit.
2. Moderately vigorous to vigorous growth habit.

3. Strong stems.
4. Large mophead-type inflorescences with red purple-colored sterile flowers that are initially light green and red purple in color during early development.

Plants of the new *Hydrangea* differ primarily from plants of the parent selections in plant habit as plants of the new *Hydrangea* are more compact and uniform than plants of the parent selections.

Plants of the new *Hydrangea* can be compared to plants of *Hydrangea macrophylla* 'Bela', disclosed in U.S. Plant Pat. No. 16,099. Plants of the new *Hydrangea* differ primarily from plants of 'Bela' in the following characteristics:

1. Plants of the *Hydrangea* are not as vigorous as plants of 'Bela'.
2. Plants of the new *Hydrangea* are more freely branching than plants of 'Bela'.
3. Leaves of plants of the new *Hydrangea* are smaller and lighter green in color than leaves of plants of 'Bela'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Saxreb13' grown in a container.

The photograph on the second sheet is a close-up view of typical fully developed inflorescences of 'Saxreb13' during the summer.

The photograph on the third sheet is a close-up view of a typical developing inflorescence of 'Saxreb13' during the spring.

DETAILED BOTANICAL DESCRIPTION

Plants used in the aforementioned photographs and in the following description were grown during the spring and summer in 3-liter containers in a glass-covered greenhouse in Dresden, Germany and under cultural practices typical of commercial *Hydrangea* production. Plants of the new *Hydrangea* were three years old when the photographs and description were taken. During the production of the plants, day temperatures ranged from 18° C. to 25° C. and night temperatures ranged from 16° C. to 17° C. Plants used for the description and photographs were not treated with aluminum sulfate to "blue" the inflorescences. In the following description, color references are made to The Royal Horticultural Society Colour Chart, 2007 Edition, except where general terms of ordinary dictionary significance are used.

Botanical description: *Hydrangea macrophylla* 'Saxreb13'.

Parentage:

*Female, or seed, parent*.—Unidentified proprietary selection of *Hydrangea macrophylla*, not patented.

*Male, or pollen, parent*.—Unidentified proprietary selection of *Hydrangea macrophylla*, not patented.

Propagation:

*Type cutting*.—By softwood cuttings.

*Time to initiate roots, summer*.—About 14 days at temperatures about 18° C.

*Time to initiate roots, winter*.—About 16 days at temperatures about 18° C.

*Time to produce a rooted young plant, summer*.—About 28 days at temperatures about 18° C.

*Time to produce a rooted young plant, winter*.—About 31 days at temperatures about 18° C.

*Root description*.—Fine, fibrous; white in color.

*Rooting habit*.—Moderately freely branching; medium density.

Plant description:

*Plant and growth habit*.—Perennial subshrub; upright and mounded plant habit; broadly inverted triangle; freely branching habit with about 18 lateral branches developing per plant; strong lateral branches; moderately vigorous to vigorous growth habit.

*Plant height*.—About 36.5 cm.

*Plant diameter or area of spread*.—About 54.8 cm.

*Lateral branches*.—Length: About 19.3 cm. Diameter: About 7 mm. Internode length: About 4.9 cm. Texture: Smooth, glabrous. Strength: Strong. Aspect: About 45° from vertical. Color, developing: Close to 143C; at the nodes, slightly tinged with close to N186C. Color, developed: Close to 199B to 199C. Lenticels: Density: Sparse. Length: About 2 mm. Diameter: About 0.75 mm. Color: Close to N186C.

Leaf description:

*Arrangement*.—Opposite, simple.

*Length*.—About 12.8 cm.

*Width*.—About 8.5 cm.

*Shape*.—Ovate to oblong.

*Apex*.—Broadly apiculate.

*Base*.—Attenuate.

*Margin*.—Serrate.

*Texture, upper and lower surfaces*.—Glabrous; slightly rugose.

*Venation pattern*.—Pinnate.

*Color*.—Developing leaves, upper surface: Close to N137B. Developing leaves, lower surface: Close to 137C. Fully expanded leaves, upper surface: Darker than between N137A and 147A; venation, close to 144B. Fully expanded leaves, lower surface: Close 137B to 137C; venation, close to 144B.

*Petioles*.—Length: About 2.6 cm. Diameter: About 4 mm. Texture, upper and lower surfaces: Smooth, glabrous. Color, upper surface: Close to 144A. Color, lower surface: Close to 144A to 144B.

Inflorescence & flower description:

*Flower type and habit*.—Showy single sterile and inconspicuous single fertile flowers arranged on terminal mophead-type panicles; panicles flattened globular in overall shape; fertile flowers face mostly upright and sterile flowers face upright to outwardly.

*Fragrance*.—None detected.

*Natural flowering season*.—Continuous flowering from late spring to late summer in Germany.

*Flower longevity, fertile flowers*.—Flowers last about one week on the plant; fertile flowers not persistent.

*Flower longevity, sterile flowers*.—Flowers last about six weeks on the plant; sterile flowers persistent.

*Quantity of flowers*.—Freely flowering; about 45 fertile flowers and about 500 sterile flowers per panicle.

*Panicle height*.—About 10.5 cm.

*Panicle diameter*.—About 16.9 cm.

*Flower diameter, fertile flowers*.—About 7 mm.

*Flower depth (height), fertile flowers*.—About 5 mm.

*Flower diameter, sterile flowers*.—About 3.2 cm.

*Flower depth (height), sterile flowers*.—About 1.2 cm.

*Flower buds, fertile flowers*.—Length: About 3 mm. Diameter: About 3 mm. Shape: Globular. Color: Close to 65C.

*Flower buds, sterile flowers*.—Length: About 1 cm. Diameter: About 5 mm. Shape: Ovoid. Color: Close to 149D; towards the apex, close to N57C.

*Petals, fertile flowers only*.—Quantity and arrangement: Five in a single whorl. Length: About 2 mm. Width: About 1.75 mm. Shape: Ovate, concave. Apex: Acute. Base: Cuneate. Margin: Entire. Texture, upper and lower surfaces: Smooth, glabrous. Color: When opening and fully opened, upper surface: Close to 65A; color does not change with development. When opening and fully opened, lower surface: Close to 65A to 65B; color does not change with development.

*Sepals, fertile flowers*.—Quantity and arrangement: Five in a single whorl. Length: About 1 mm. Width: About 0.1 mm. Shape: Deltoid. Apex: Acute. Base: Broadly cuneate. Margin: Entire. Texture, upper and lower surfaces: Smooth, glabrous. Color: When opening, upper and lower surfaces: Close to 145B to 145C tinged with close to 62D. Fully opened, upper and lower surfaces: Close to 145B to 145C tinged with close to 62D; color does not change with development.

*Sepals, sterile flowers*.—Quantity and arrangement: Four in a single whorl. Length: About 1.8 cm. Width: About 2 cm. Shape: Broadly rhomboidal to broadly ovate. Apex: Bluntly acute. Base: Broadly cuneate. Margin: Entire. Texture, upper and lower surfaces: Smooth, glabrous. Color: When opening, upper surface: Proximally, close to 145B to 145D; transitions distally, close to 58D to 58B; with development, proximally, color becoming closer to NN155D. When opening, lower surface: Proximally, close to 145C to 145D; transitions distally, close to lighter than 61D to close to 61D. Fully opened, upper surface: Close to between 58B and 61C; color does not change with development. Fully opened, lower surface: Close to 62A; color does not change with development.

*Pedicels, fertile flowers*.—Angle: About 20° from vertical. Strength: Moderately strong. Length: About 2 mm. Diameter: About 0.75 mm. Texture: Smooth, glabrous. Color: Close to 62B.

*Pedicels, sterile flowers*.—Angle: About 40° from lateral branch. Strength: Strong. Length: About 1.5 cm. Diameter: About 1 mm. Texture: Smooth, glabrous. Color: Close to 62A to 62B.

*Reproductive organs, fertile flowers*.—Stamens: Quantity per flower: About ten. Filament length: About 3 mm. Filament color: Close to 157D. Anther length: About 1 mm. Anther shape: Broadly reniform. Anther color: Close to 155A. Pollen amount: None observed. Pistils: Pistil quantity per flower: About two. Pistil length: About 1.75 mm. Stigma shape: Club-shaped. Stigma color: Close to 155D. Style length: About 0.75 mm. Style color: Close to 69A to 69B. Ovary color: Close to 145C to 145D.

*Reproductive organs, sterile flowers*.—Stamens: Quantity per flower: About eight. Filament length: About 1.5 mm. Filament color: Close to 157D. Anther length: About 0.5 mm. Anther shape: Broadly reniform. Anther color: Close to 155A. Pollen amount: None observed. Pistils: Pistil quantity per flower: About two. Pistil length: About 1 mm. Stigma shape: Club-shaped. Stigma color: Close to 161B. Style length: About 0.5 mm. Style color: Close to 161D. Ovary color: Close to 157D.

*Seeds and fruits*.—To date, seed and fruit development have not been observed on plants of the new *Hydrangea*.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures in USDA Hardiness Zones 5 to 9.

It is claimed:

1. A new and distinct *Hydrangea* plant named 'Saxreb13' as illustrated and described.

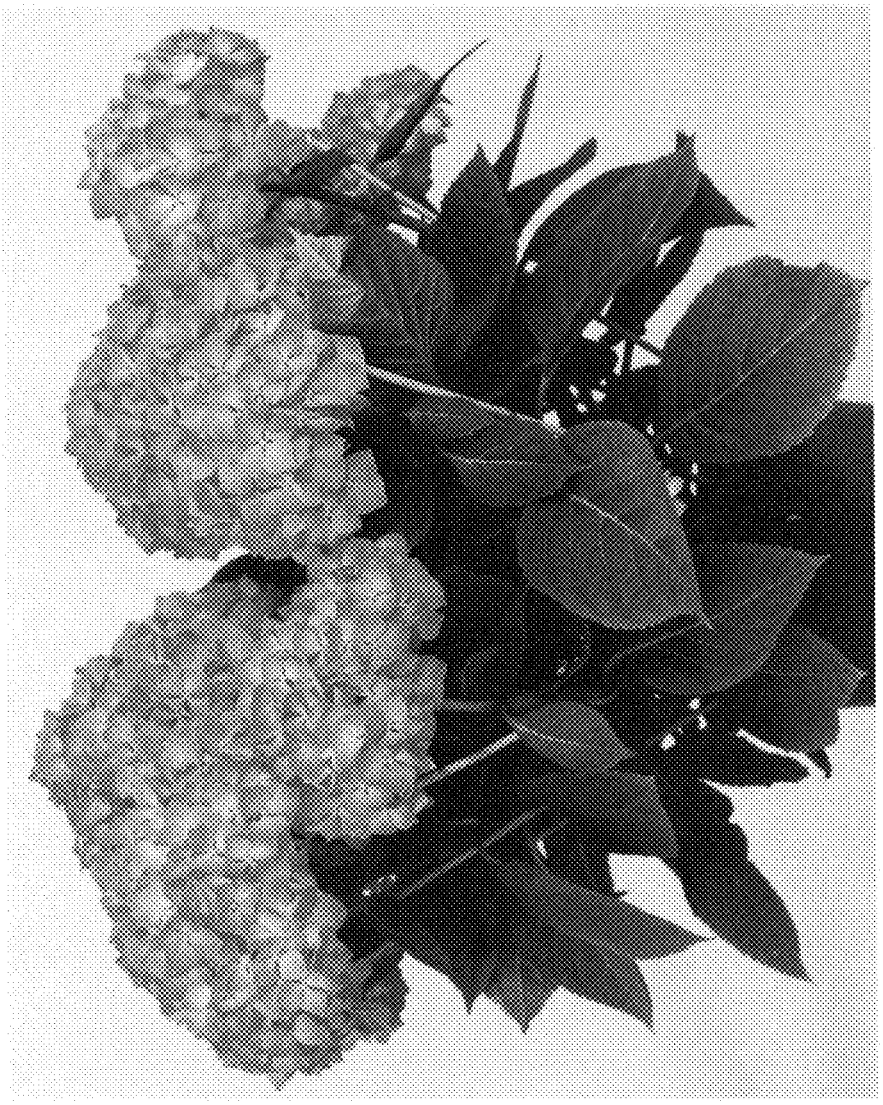

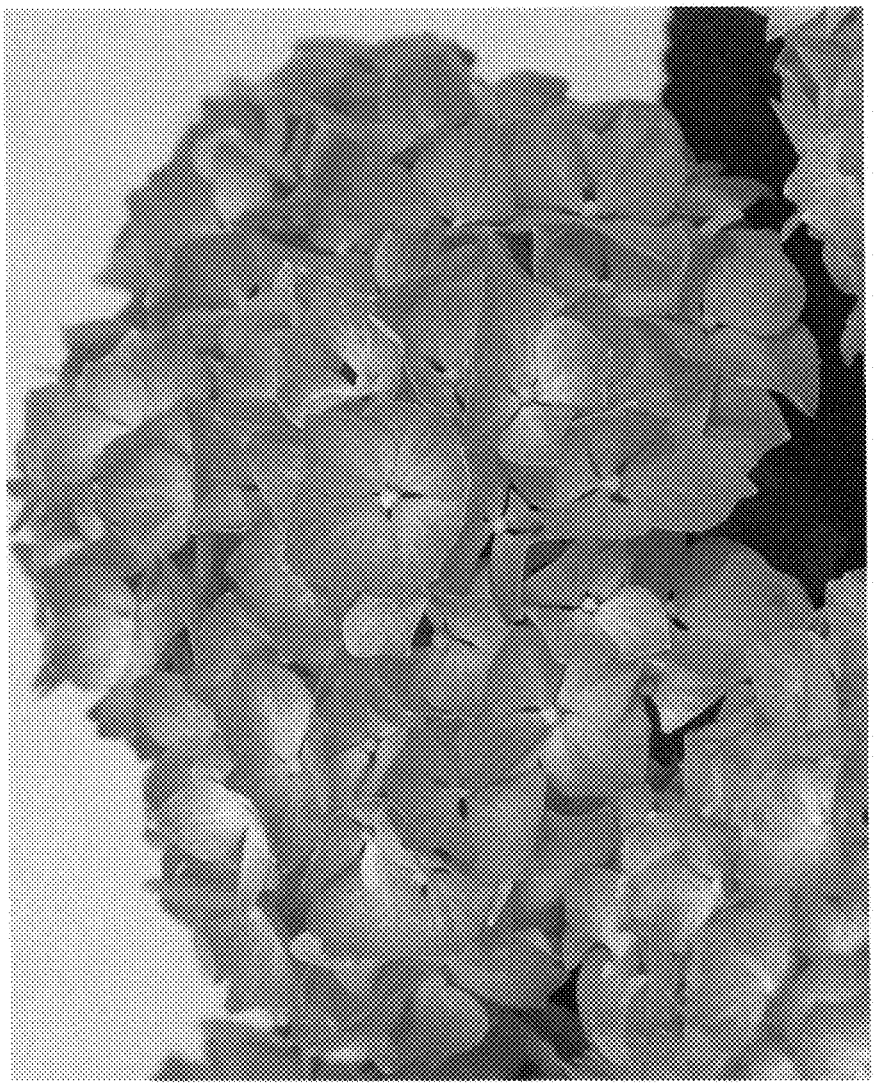

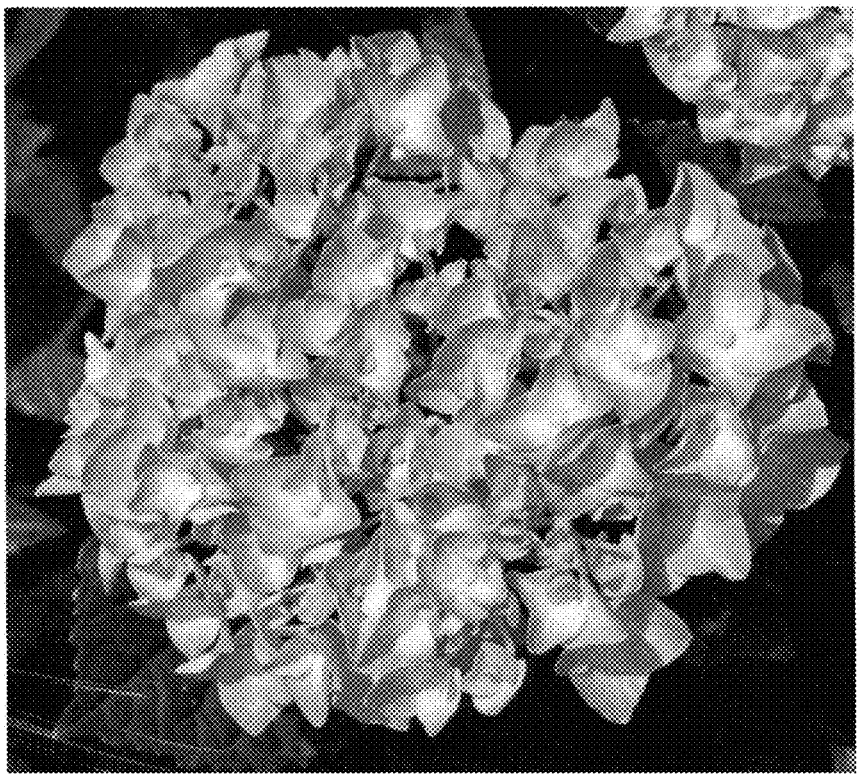

* * * * *